United States Patent [19]
Aoyama et al.

[11] Patent Number: 5,186,809
[45] Date of Patent: Feb. 16, 1993

[54] STRUCTURE FOR JOINING A WIRE TO A SOLID ELECTROLYTIC ELEMENT

[75] Inventors: Toshihiko Aoyama, Seto; Haruhisa Shiomi, Kyoto; Yasuhiro Ujita, Kasugai, all of Japan

[73] Assignee: NGK Spark Plug Co., Ltd., Nagoya, Japan

[21] Appl. No.: 794,663

[22] Filed: Nov. 18, 1991

Related U.S. Application Data

[63] Continuation of Ser. No. 697,747, May 6, 1991, which is a continuation of Ser. No. 430,694, Nov. 1, 1989.

[30] Foreign Application Priority Data

Nov. 2, 1988 [JP] Japan ................. 63-278115

[51] Int. Cl.⁵ .............. G01N 27/406; G01N 27/407
[52] U.S. Cl. ..................... 204/421; 204/427; 204/429
[58] Field of Search ............ 204/153.18, 421, 424–429

[56] References Cited

U.S. PATENT DOCUMENTS

| | | | |
|---|---|---|---|
| 3,616,413 | 10/1971 | Reichner | 204/428 |
| 3,843,400 | 10/1974 | Radford et al. | 204/427 |
| 4,310,401 | 1/1982 | Stahl | 204/426 |
| 4,334,974 | 6/1982 | Muller et al. | 204/425 |
| 4,502,939 | 3/1985 | Holfelder et al. | 204/425 |
| 4,668,375 | 5/1987 | Kato et al. | 204/426 |
| 4,769,123 | 9/1988 | Mase et al. | 204/426 |

OTHER PUBLICATIONS

*Hackh's Chemical Dictionary*, 4th ed., (1969), p. 623.

*Primary Examiner*—T. Tung
*Attorney, Agent, or Firm*—Sughrue, Mion, Zinn, Macpeak & Seas

[57] ABSTRACT

In the joining structure of the solid electrolytic element, terminals connected to the heating element and the electrodes are attached through metallic oxide layers onto the solid electrolytic layer. The thermal conductivity coefficient of the metallic oxide layers is larger than that of the solid electrolytic layer. The thermal expansion coefficient of the metallic oxide layers is the same as or smaller than that of the solid electrolytic layer. Consequently, when the lead wires are soldered to the terminals, heat is quickly conducted to the terminals, enhancing the fluidity and the solderability of the soldering material. Since excess heating is not required for soldering, the solid electrolytic layer is prevented from deteriorating due to heat. Since a low-melting solder is not used, the joining structure has high heat resistance. Moreover, during soldering, the metallic oxide layers do not detach from the solid electrolytic layer due to heat.

22 Claims, 4 Drawing Sheets

STRUCTURE FOR JOINING A WIRE TO A SOLID ELECTROLYTIC ELEMENT

This is a continuation of application No. 07/697,747 filed May 6, 1991 which was a continuation of application Ser. No. 07/430,694 filed Nov. 1, 1989.

BACKGROUND OF THE INVENTION

This invention relates to a joining structure of a solid electrolytic element, especially of a solid electrolytic element used for an oxygen sensor.

Conventionally, a solid electrolytic detecting element is applied to an oxygen sensor for detecting the concentration of oxygen in gas. The solid electrolytic element is composed of a solid electrolytic panel which generates electromotive force due to its difference in oxygen concentration from that of the ambient atmosphere. A measuring electrode is provided on the surface of the solid electrolytic panel that faces the gas to be measured. A reference electrode is provided opposite to the measuring electrode. The measuring and the reference electrodes are connected, respectively, via electron conducting layers to output terminals on the end of the solid electrolytic panel. Around the electrodes there are heating elements which stabilize output by heating the solid electrolytic panel. The heating element is connected via electron conducting layers to heating terminals.

Lead wires, generally made of stainless or tin-plated copper, are connected respectively to the output terminals and the heating terminals so as to deliver output or to apply voltage.

Various joining structures of the solid electrolytic element have been proposed. The platinum lead wires are fixed to the terminals, for example, by using platinum paste or high-temperature solder, by sintering the platinum wires together with ceramic, or by plug engagement. However, these related-art joining methods cannot assure high reliability.

Another joining structure has been proposed in which the lead wires are directly soldered to the terminals on the surface of the solid electrolytic panel. This structure has high joining strength as well as high heat resistance. However, since the solid electrolytic panel has a small coefficient of thermal conductivity, it is hard to lower the gradient of the temperature of the terminals uniformly. When the temperature of the terminals lowers, the fluidity of soldering material is impaired, reducing the joining strength of the terminals and the lead wires. On the other hand, when the soldering temperature is raised to improve the fluidity of the soldering material, heat adversely affects the solid electrolytic panel because the reducing gas resulting in soldering disperses oxygen ions from solid electrolyte, which makes the solid electrolytic panel dark. When soldering material with a low melting temperature is applied to avoid the deterioration of the solid electrolyte due to high temperature, the heat resistance of the joining structure is deteriorated.

SUMMARY OF THE INVENTION

The object of the present invention is to provide a joining structure of a solid electrolytic element which assures proper soldering of lead wires to terminals.

This object is achieved by the present invention, which provides a structure for attaching a wire to a solid electrolytic element. The solid electrolytic element comprises a solid electrolytic layer, a metallic oxide layer formed on a surface of the solid electrolytic layer, and terminal means attached to the metallic oxide layer for attaching a wire to the solid electrolytic layer. The metallic oxide layer has a thermal conductivity coefficient larger than the thermal conductivity coefficient of the solid electrolytic layer and a thermal expansion coefficient not greater than the thermal expansion coefficient of the solid electrolytic layer.

The solid electrolytic layer, which conducts oxygen ions, is composed of zirconium oxide-yttrium oxide ($ZrO_2$-$Y_2O_3$) or zirconium oxide-calcium oxide ($ZrO_2$-$CaO$).

The heating element, which is provided around the electrodes, is composed of tungsten or platinum containing ceramic.

Like the heating elements, the electrodes and the terminals are composed of platinum containing ceramic.

The metallic oxide layers are composed of material whose thermal conductivity coefficient is larger than that of the solid electrolytic layer and whose thermal expansion coefficient is the same as or smaller than that of the solid electrolytic layer. According to the material of the solid electrolytic layer, the metallic oxide layers can be composed of ceramic such as alumina, or spinel. When the solid electrolyte is composed of $ZrO_2$-$Y_2O_3$, alumina is best to assure a suitable thermal conductivity coefficient as well as a suitable thermal expansion coefficient. The metallic oxide layers should be 5 to 300 microns thick so as to easily conduct heat during soldering.

DETAILED DESCRIPTION OF THE PREFERRED EMBODIMENT

Figure 1:
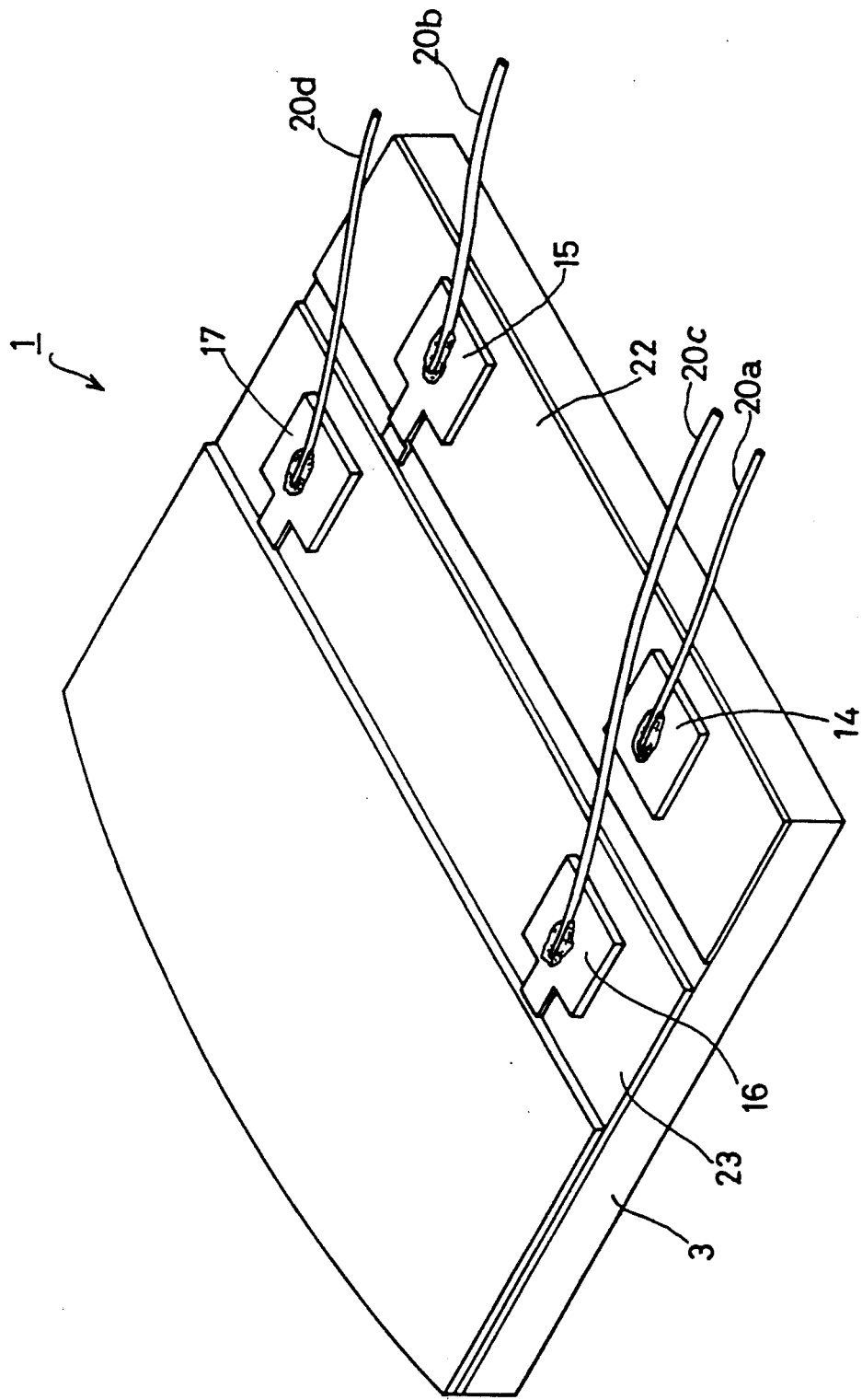
FIG. 1 is a perspective view developing the rear part of a solid electrolytic element.

An embodiment of the present invention is explained referring to the drawings.

Figure 2:
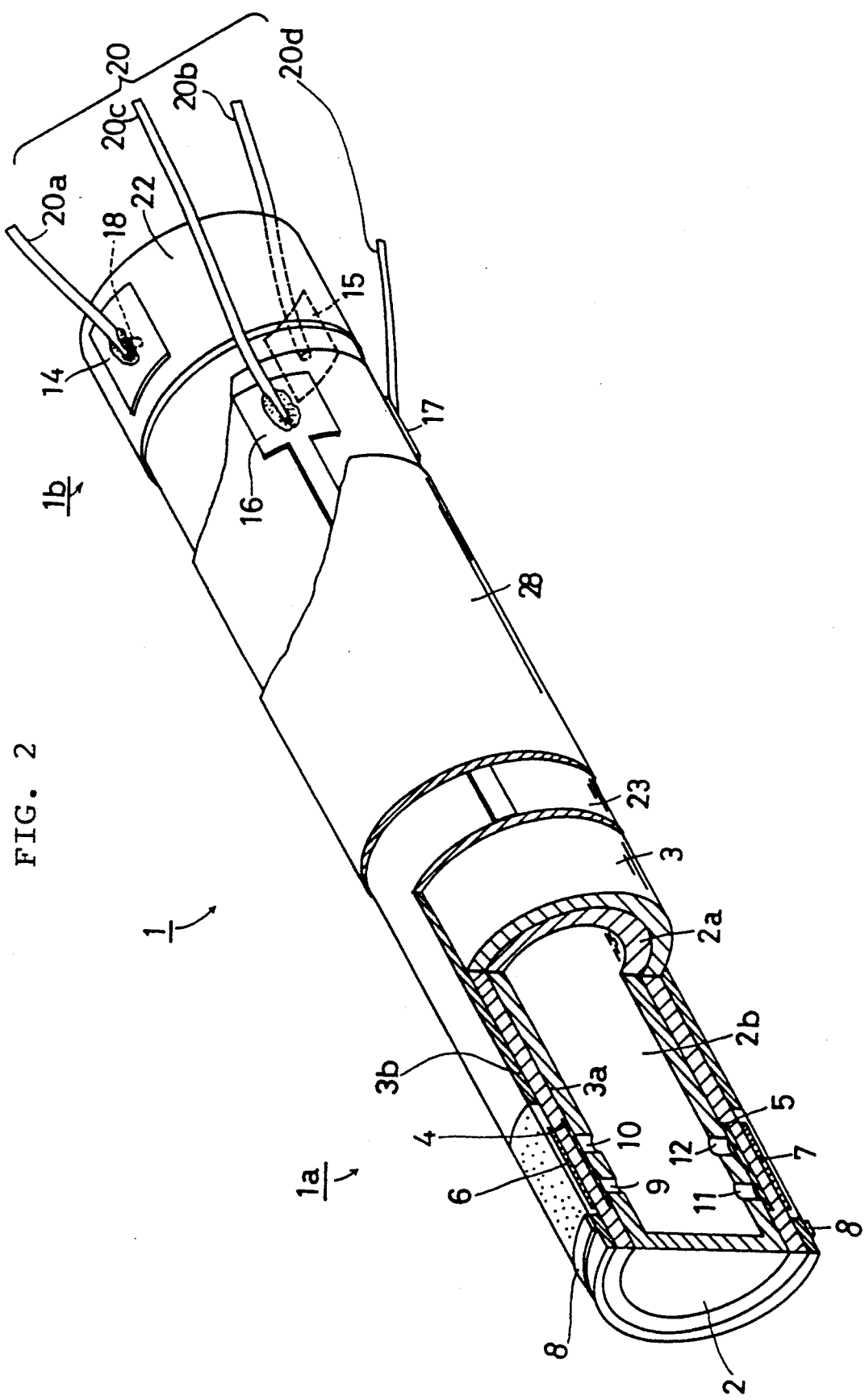
FIG. 2 is a partially cut perspective view of the solid electrolytic element.

As shown in FIG. 2, a solid electrolytic element 1, which is used for an oxygen sensor, comprises a cylindrical ceramic body 2 with one end closed and a solid electrolytic layer 3 formed on the surface of the cylindrical ceramic body 2. The cylindrical ceramic body 2 is composed of stabilized or partially stabilized zirconia, and the solid electrolytic layer 3 is composed of $ZrO_2$-$Y_2O_3$ solid solution.

At a front end 1a of the solid electrolytic element 1, first and second reference electrode portions 4, 5, (hereinafter referred to as "first and second reference electrodes 4,5") and first and second measuring electrode portions 6, 7 (hereinafter referred to as "first and second measuring electrodes 6,7) are provided, respectively, on the opposite sides of the solid electrolytic layer 3 to detect gas to be measured.

Specifically, the first and second reference electrodes 4, 5, composed of platinum containing zirconia, are provided on an inner periphery 3a of the solid electrolytic layer 3 adjacent to a side wall 2a of the cylindrical ceramic body 2. On the other hand, the first and second measuring electrodes 6, 7, composed of platinum containing zirconia, are provided on an outer periphery 3b of the solid electrolytic layer 3, and are opposed to the first and second reference electrodes 4, 5, respectively. A heating element 8, composed of platinum containing alumina, is provided adjacent to the first and second measuring electrodes 6, 7. First through fourth through holes 9, 10, 11, 12 are provided in the side wall 2a, and connect a hollow 2b and the first and second reference electrodes 4, 5.

The first through fourth through holes 9, 10, 11, 12 introduce atmospheric air from the hollow 2b of the cylindrical ceramic body 2 to the solid electrolytic layer 3. The first and second through holes 9, 10 are opposed to the third and fourth through holes 11, 12, respectively.

On the other hand, a reference-electrode terminal 14, a measuring-electrode terminal 15 and a pair of heating terminals 16, 17, which are composed of platinum containing zirconia, are formed on a rear end 1b of the solid electrolytic element 1. The reference-electrode terminal 14 is connected via a through hole 18 in the solid electrolytic layer 3 to the first and second reference electrodes 4, 5. The measuring-electrode terminal 15 is connected to the first and second measuring electrodes 6, 7, and the heating terminals 16, 17 are connected to the heating element 8.

Lead wires 20a and 20b are soldered, respectively, to the reference-electrode terminal 14 and the measuring-electrode terminal 15 to carry output from the terminals 14 and 15. Lead wires 20c and 20d are soldered, respectively, to the heating terminals 16 and 17 to apply voltage to the terminals 16 and 17.

As shown in FIG. 1, a first intermediate layer 22 is formed between the solid electrolytic layer 3 and the reference-electrode and measuring-electrode terminals 14, 15. The first intermediate layer 22 is from ten to fifty microns thick and is composed of alumina whose thermal conductivity coefficient is 0.1 to 0.2 cal/cm sec.° C. and whose thermal expansion coefficient is $7 \times 10^{-6}/°$ C. to $8 \times 10^{-6}/°$ C. A second intermediate layer 23 is formed between the solid electrolytic layer 3 and the heating terminals 16, 17. The second intermediate layer 23 is from ten to fifty microns thick and is composed of alumina. As shown in FIG. 2, the second intermediate layer 23 extends to the front end 1a of the solid electrolytic element 1 and functions as an insulating layer between the heating element 8 and the solid electrolytic layer 3.

Figure 3A:
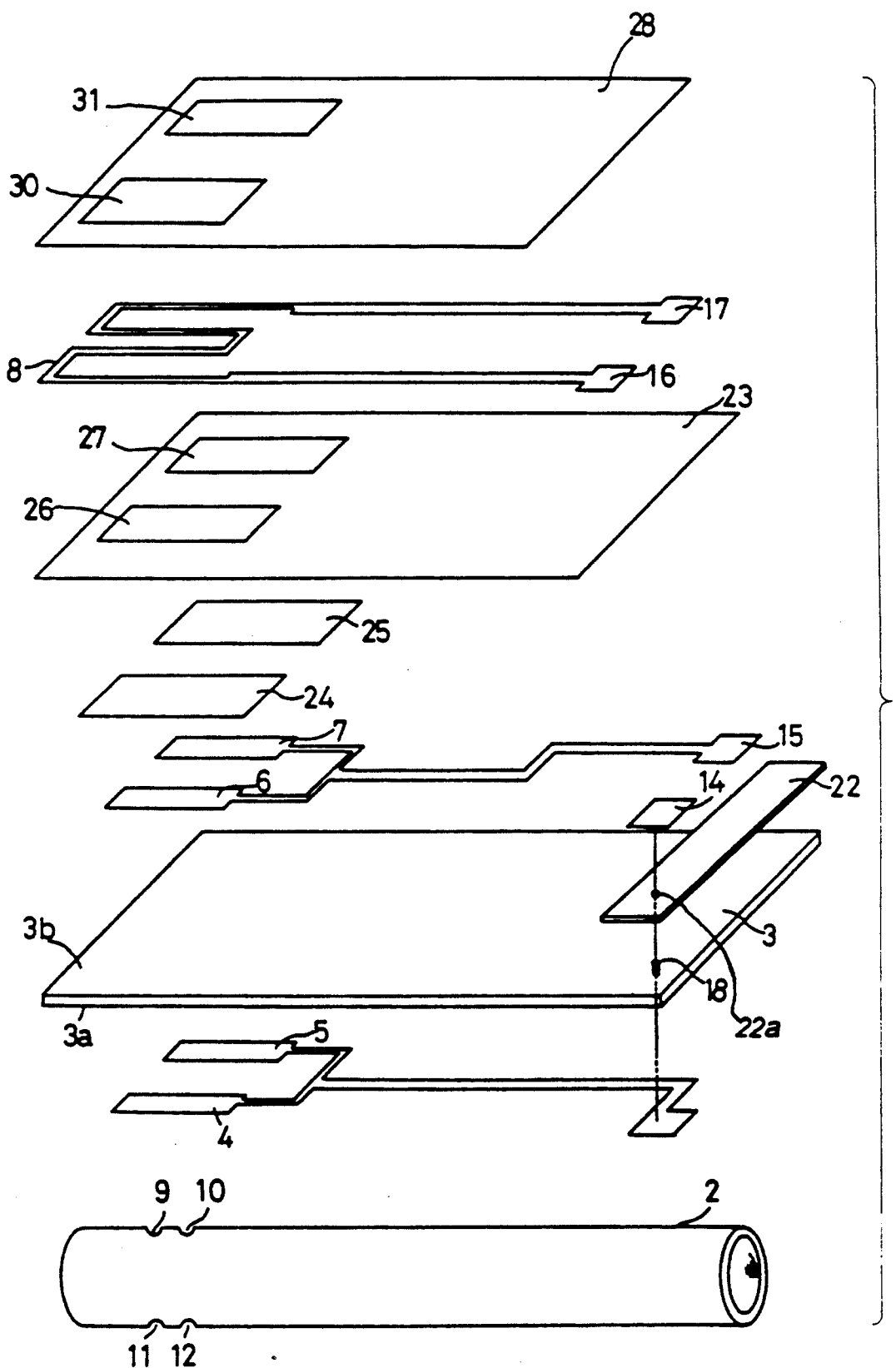
FIG. 3A is an exploded view of the solid electrolytic element.

The method for manufacturing the solid electrolytic element is explained referring to FIG. 3A.

The cylindrical ceramic body 2 is formed in a metal mold or extruded through the metal mold, and is sintered.

The solid electrolytic layer 3 is composed of green sheet, which is compressed, powdered metallic oxide prior to sintering, as will be more fully explained below. The green sheet is manufactured by mixing 10% to 20% of binder into raw ceramic powder of $ZrO_2$-$Y_2O_3$ solid solution.

Subsequently, the first and second reference electrodes 4 and 5, which are ten micron thick films composed of platinum containing zirconia, are printed on the inner periphery 3a of the solid electrolytic layer 3 comprising the rear face of the green sheet.

On the other hand, the first intermediate layer 22, which is a film composed of alumina containing 15% to 25% of binder, is printed on the end of the outer periphery 3b of the solid electrolytic layer 3 comprising the surface of the green sheet.

Figure 3B:
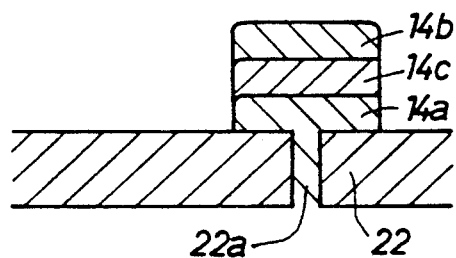
FIGS. 3B, 3C and 3D are cross-sectional views of terminals, electrodes and intermediate layers of the solid electrolytic element.
Figure 3C:
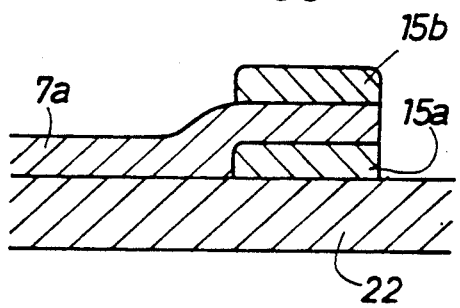

The reference-electrode terminal 14 and the measuring-electrode terminal 15, each including ten microns thick films composed of platinum containing alumina, are printed on the surface of the first intermediate layer 22. The first and second measuring electrodes 6, 7, which are ten microns thick films composed of platinum containing zirconia ceramics, are printed on the outer periphery 3b of the solid electrolytic layer 3. As shown in FIGS. 3B and 3C, the upper film layer 14b of the reference-electrode terminal 14 and the upper film layer 15b of the measuring-electrode terminal 15 are ten microns thick and are composed of platinum containing less than 10% of alumina or less than 10% of zirconia. A layer 14c is between the upper film layer 14b and a lower film layer 14a printed on the intermediate layer 22 having a through hole 22a leading to the hole 18. As shown in FIG. 3C, a measuring electrode 7a, which is a ten microns thick film and of the same composition as measuring electrodes 6, 7, extends from the first and second measuring electrodes 6, 7 to between upper and lower film layers 15a and 15b of the measuring electrode terminal 15. Lower film layer 15a is formed on the surface of the first intermediate layer 22. The lower film layers 14a and 15a are composed of platinum paste containing from 20% to 60%, preferably 40%, of alumina. Layer 14c is formed of the same composition as that of measuring electrode 7a. The upper film layers 14b and 15b can be composed of platinum paste containing less than 10% of zirconia. They can be composed of paste containing pure platinum. The upper and lower film layers 14a, 14b, 15a, 15b can be composed of platinum paste containing a metallic oxide chosen from alumina, magnesia, or spinel. The metallic oxide contained in the above layers is preferably the same as that chosen for the intermediate layer 22.

Subsequently, protecting layers 24, 25, which are twenty micron thick films composed mainly of alumina, are printed on the surface of the first and second measuring electrodes 6, 7.

The second intermediate layer 23, which is a thirty micron thick film composed of alumina, is printed on the surface of the green sheet. However, the second intermediate layer 23 does not cover the reference-electrode terminals 14 and 15 on the green sheet. Since the second intermediate layer 23 has first windows 26 and 27 in it, it does not cover the first and second measuring electrodes 6 and 7.

Figure 3D:
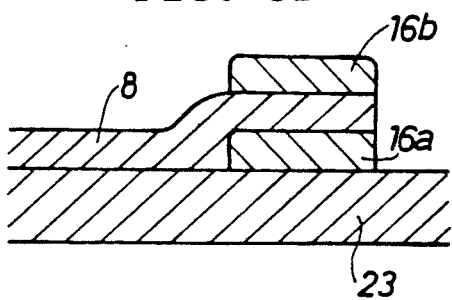

Subsequently, lower film layers 16a and 17a of the heating terminals 16 and 17 are printed on the surface of the second intermediate layer 23. Heating terminals 16 and 17 are the same and only heating terminal 16 is illustrated in FIG. 3D. The lower film layers 16a and 17a are ten microns thick and are composed of platinum containing from 20% to 60% of alumina similar to the lower film layers 14a and 15a. The upper film layers 16b and 17b are printed on the heating element 8 on the lower film layers 16a and 17a. The upper film layers 16b and 17b, which are composed of platinum containing less than 10% of alumina or containing less than 10% of zirconia, are printed on the heating element 8. They can also be composed of paste containing pure platinum. The upper and lower film layers 16a, 16b, 17a, 17b can be composed of platinum paste containing a metallic oxide chosen from alumina, magnesia, or spinel. The metallic oxide contained in heating terminals 16, 17 is preferably the same as the metallic oxide chosen for the second intermediate layer 23.

An insulating layer 28, which is a twenty micron thick film composed of alumina containing silica, is printed on the surface of the second intermediate layer 23. However, the insulating layer 28 does not overlap the heating terminals 16 and 17. Since the insulating layer 28 has second windows 30 and 31 in it, it does not overlap the first and second measuring electrodes 6 and 7.

Zirconia paste is applied to the rear face of the film-printed green sheet. The green sheet is coated on the outer periphery of the cylindrical ceramic body 2 so that the first and second reference electrodes 4 and 5 correspond to the two pairs of the first through fourth through holes 9, 10, 11, 12, respectively. The green sheet is attached to the outer periphery of the cylindrical ceramic body 2, the outer surface of the cylindrical ceramic body 2 is pressed using rubber tube while evacuating the inside of the rubber tube, and the green sheet is thus fixed onto the cylindrical ceramic body 2. Finally, the cylindrical ceramic body 2 with the green sheet fixed thereon is sintered under atmospheric pressure.

After sintering the cylindrical ceramic body 2, lead wires 20 are soldered to the reference-electrode terminal 14, the measuring-electrode terminal 15, and the heating terminals 16, 17 by using silver solder. When temperature of terminals 16 and 17 rises more than 350°C., the gold solder should preferably be used. The silver solder consists of 72% of silver and 28% of copper, the specification of the silver solder is BAG8 according to JIS, and the melting point of the silver solder is 789° C. By heating the silver solder at about 850° C. for about ten minutes, the lead wires 20 are soldered to the terminals 14, 15, 16, 17, completing the joining structure of the solid electrolytic element 1.

The thermal conductivity coefficient of alumina composing the first and second intermediate layers 22 and 23 is larger than that (i.e. 0.05 cal/cm.sec.° C.) of $ZrO_2$-$Y_2O_3$ solid solution composing the solid electrolytic layer 3. When the lead wires 20 are soldered to the reference-electrode terminal 14, the measuring-electrode terminal 15 and the heating terminals 16, 17 by heating, heat is quickly and uniformly conducted to the terminals 14, 15, 16, 17 and the surrounding first and second intermediate layers 22 and 23, improving the fluidity of the solder and assuring firm soldering.

The thermal expansion coefficient of the $ZrO_2$-$Y_2O_3$ solid solution is between $9 \times 10^{-6}/°$ C. and $10 \times 10^{-6}/°$ C. The thermal expansion coefficient of alumina composing the first and second intermediate layers 22 and 23 is smaller than that of the $ZrO_2$-$Y_2O_3$ solid solution composing the solid electrolytic layer 3. When the first and second intermediate layers 22 and 23 are rapidly heated to high temperature during soldering, the dimension of the layers 22 and 23 does not deviate from that of the solid electrolytic layer 3. The layers 22 and 23 are thus prevented from detaching from the solid electrolytic layer 3 due to thermal expansion.

Since the lead wires 20 can be firmly soldered to the reference-electrode terminal 14, the measuring-electrode terminal 15, and the heating terminals 16 and 17 without excess heating the solid electrolytic layer 3 is prevented from deteriorating due to the heat used for soldering. In addition, the temperature of about 850° C. assures an effective solder, because low-melting solder does not need to be used. The heat resistance of the solid electrolytic element 1 is thus enhanced.

Although the specific embodiment of the invention has been shown and described for the purpose of illustration, the invention is not limited to the embodiment illustrated and described. This invention includes all embodiments and modifications that come within the scope of the claims.

For example, the second intermediate layer 23 can be divided into two parts for the heating element 8 and the solid electrolytic layer 3. The first and second intermediate layers 22 and 23 can cover only the reference-electrode terminal 14 and the measuring-electrode terminal 15, and the heating terminals 16 and 17, respectively. The second intermediate layer 23, which is between the heating element 8 and the solid electrolytic layer 3, can be also provided between third and fourth electrodes 6, 7 and the solid electrolytic layer 3.

We claim:

1. A structure for attaching a wire to a solid electrolytic element with solder, comprising:

a solid electrolytic element;

an intermediate layer formed on a surface of the solid electrolytic element;

terminal means attached to the intermediate layer for attaching a wire to the solid electrolytic element, said terminal means comprising a base layer and an upper layer, wherein the base layer is adjacent to the intermediate layer and contains a larger amount of the composition of the intermediate layer than the upper layer which is not adjacent to the intermediate layer, said terminal means comprising a plurality of terminals, wherein at least one of said plurality of terminals is electrically connected to a plurality of electrode portions formed on a surface of the solid electrolytic element, said plurality of electrode portions including first and second measuring electrode portions;

means for heating said solid electrolytic element, wherein said terminal means includes two heating terminals electrically connected to said heating means; and an outer insulating layer positioned over said heating means such that said two heating terminals are not overlapped by said outer insulating layer, said outer insulating layer having a plurality of windows positioned over said first and second measuring electrode portions such that said first and second measuring electrode portions are not overlapped by said outer insulating layer;

wherein said base layer of said terminal means includes 20% to 60% of the same material as that of which said intermediate layer is composed, and said upper layer of said terminal means includes less than 10% of the same material as that of which said intermediate layer is composed;

wherein the intermediate layer has a thermal conductivity coefficient larger than the thermal conductivity coefficient of the solid electrolytic element so that heat is uniformly conducted to said terminal means and said intermediate layer, thereby to ensure the fluidity of said solder, and a thermal expansion coefficient not greater than the thermal expansion coefficient of the solid electrolytic element so that said intermediate layer has dimensions which do not deviate from those of said solid electrolytic element and is prevented from detaching from said solid electrolytic layer due to thermal expansion thereof.

2. The structure of claim 1, wherein the solid electrolytic element is composed of $ZrO_2$-$Y_2O_3$ solid solution.

3. The structure of claim 2, wherein the wire is attached to the terminal means using a silver solder.

4. The structure of claim 1, wherein the intermediate layer is composed of spinel, or alumina.

5. The structure of claim 3, wherein the intermediate layer is between 5 and 300 microns thick.

6. The structure of claim 3, wherein the intermediate layer is between 10 and 50 microns thick.

7. The structure of claim 1, wherein the terminal means is composed of platinum containing a metallic oxide chosen from the group consisting of zirconia and alumina.

8. The structure of claim 1, wherein a plurality of intermediate layers are formed on the surface of the solid electrolytic element and one or more terminal means are attached to at least one of the plurality of intermediate layers.

9. The structure according to claim 7, further comprising a plurality of protective layers formed on surfaces of said first and second measuring electrode portions.

10. The structure according to claim 9, wherein a first intermediate layer of said plurality of intermediate layers includes a plurality of windows formed therein such that said first and second measuring electrode portions are not overlapped by said first intermediate layer, said protective layers covering said first and second measuring electrode portions being exposed through said windows of said first intermediate layer.

11. The structure of claim 1, wherein the solid electrolytic element is composed of $ZrO_2$-$Y_2O_3$ solid solution.

12. The structure of claim 1, wherein the two heating terminals and the heating means are formed on a single intermediate layer.

13. The structure of claim 12, wherein the single intermediate layer on which the heating means is formed electrically insulates the heating means from the solid electrolytic element.

14. The structure of claim 1, wherein the wire is soldered to the terminal means of the heating means with silver solder.

15. The structure of claim 1, where:
the base layer is formed on the surface of the intermediate layer and is composed of platinum containing spinel or alumina;
an electrode portion is formed on the base layer;
the upper layer is formed on the electrode portion and is composed of platinum containing a metallic oxide chosen from the group consisting of zirconia and alumina.

16. The structure of claim 15, wherein the intermediate layer on which the base layer is formed is composed of alumina.

17. The structure of claim 1, wherein the electrode portions are composed of platinum containing zirconia.

18. The structure of claim 1, wherein the two heating terminals that are electrically connected to the heating means comprise at least a base layer and an upper layer, where:
the base layer is formed on the surface of the intermediate layer and is composed of platinum containing spinel, or alumina;
the heating means is formed on the base layer; and
the upper layer is formed on the heating means and is composed of platinum containing a metallic oxide chosen from the group consisting of zirconia and alumina.

19. The structure of claim 18, wherein the intermediate layer on which the heating terminals are formed is composed of the metallic oxide contained in the heating terminals.

20. The structure of claim 1, wherein the heating means is composed of platinum containing ceramics.

21. The structure of claim 1, wherein the intermediate layer is a film composed of alumina.

22. The structure of claim 1, wherein the wire is attached to the terminal means using a gold solder.

* * * * *